United States Patent [19]

Numasaki et al.

[11] Patent Number: 4,886,818

[45] Date of Patent: * Dec. 12, 1989

[54] INHIBITING GROWTH OF TUMORS WITH CERTAIN SUBSTITUTED PHENOXY DIMETHYL ACIDS, ESTERS OR SALTS

[75] Inventors: Yōsō Numasaki, Saitama; Kōichirō Takahashi, Tokyo; Isao Ohata, Saitama, all of Japan

[73] Assignee: Yamanouchi Pharmaceutical Co., Ltd., Tokyo, Japan

[*] Notice: The portion of the term of this patent subsequent to Jul. 19, 2005 has been disclaimed.

[21] Appl. No.: 198,099

[22] Filed: May 24, 1988

Related U.S. Application Data

[63] Continuation of Ser. No. 874,547, Jun. 16, 1986, Pat. No. 4,758,580.

[30] Foreign Application Priority Data

Jun. 26, 1985 [JP] Japan .................................. 60-140901

[51] Int. Cl.$^4$ ................... A61K 31/44; A61K 31/435; A61K 31/415
[52] U.S. Cl. ................................. 514/345; 514/277; 514/398; 514/399
[58] Field of Search ................. 514/345, 277, 398, 399

[56] References Cited

U.S. PATENT DOCUMENTS 4,758,580 7/1988 Wumasaki et al. .................. 514/277

*Primary Examiner*—Jerome D. Goldberg
*Attorney, Agent, or Firm*—Burgess, Ryan & Wayne

[57] ABSTRACT

This disclosure describes compositions of matter useful as growth inhibitors of transplanted tumors in mammals; and this invention discloses a method of inducing the regression and/or palliation of various types of tumors in mammals and which are susceptible to treatment by certain substituted phenoxy dimethyl alkanoic acids, esters or salts, said method comprising giving to said mammals an effective amount of a compound of the following formula:

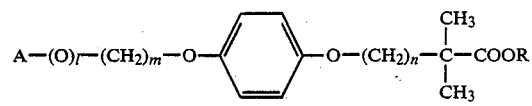

[wherein
A represents an imidazolyl group or a pyridyl group,
l represents 0 or 1,
m and n each, which may be the same or different, represents an integer of 1 to 6, and,
R represents a hydrogen atom or a lower alkyl group], or a salt thereof; the invention also discloses a method of inhibition (or prevention) of metastasis of the various cancers.

The above formula compounds have low toxicity, and it is expected to apply various types of administration thereof such as oral administration and parenteral administration.

4 Claims, No Drawings

INHIBITING GROWTH OF TUMORS WITH CERTAIN SUBSTITUTED PHENOXY DIMETHYL ACIDS, ESTERS OR SALTS

This is a continuation of application Ser. No. 874,547, filed Jun. 16, 1986 now U.S. Pat. No. 4,758,580.

BRIEF SUMMARY OF THE INVENTION

This invention relates to a method of inducing the regression and/or palliation of certain types of tumors in mammals and which are susceptible to treatment by certain substituted phenoxy dimethyl alkanoic acids, esters or salts, said method comprising administering to said mammals an effective amount of a compound of the formula

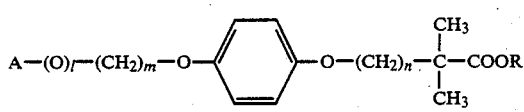

[wherein
A represents an imidazolyl group or a pyridyl group,
l represents 0 or 1,
m and n each, which may be the same or different, represents an integer of 1 to 6, and,
R represents a hydrogen atom or a lower alkyl group], or a salt thereof; the invention also relates to a method of inhibition of metastasis of the various tumors, which tumors are susceptible to treatment with certain substituted phenoxy dimethyl alkanoic acids, esters or salts.

BACKGROUND OF THE INVENTION

Among the compounds which fall under the general formula described above, some of ω-(p-substituted phenoxy)-2,2-dimethylalkanoic acid esters are described in Published Unexamined Japanese Patent Application 6667-85 or EP pat. appln. pub. No. 130,077 together with physical data thereof and are known. In the patent application supra, mention is made of utility of these compounds as medicines that they possess excellent activity of inhibiting platelet agglutination.

DETAILED EXPLANATION OF THE INVENTION

This invention relates to a method of inducing the regression and/or palliation of certain types of tumors which are susceptible to treatment by certain substituted phenoxy dimethyl alkanoic acids, esters or salts, said method comprising administering to said mammals an effective amount of a compound of the formula

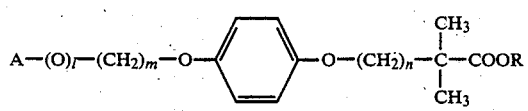

[wherein
A represents an imidazolyl group or a pyridyl group,
l represents 0 or 1,
m and n each, which may be the same or different, represents an integer of 1 to 6, and,
R represents a hydrogen atom or a lower alkyl group], or a salt thereof; the invention also relates to a method of inhibition of metastasis of those cancers susceptible to treatment with certain substituted phenoxy dimethyl alkanoic acids, esters or salts comprising administering to mammals the above compounds.

In the definition of the groups appearing in the formulae in the specification, the term "lower" refers to a straight or branched carbon chain having 1 to 5 carbon atoms, preferably 1 to 3 carbon atoms. Accordingly, specific examples of lower alkyl groups include a methyl group, an ethyl group, a propyl group, an isopropyl group, a butyl group, an isobutyl group, a sec-butyl group, a tert-butyl group, a pentyl (or amyl) group, an isopentyl group, a neopentyl group, a tert-pentyl group, etc.

The compounds represented by general formula (I) described above form salts, which the present invention encompasses.

In particular, preferred examples of the salts include salts with inorganic acids such as hydrochloric acid, hydrobromic acid, phosphoric acid, etc.; salts with organic acids such as formic acid, acetic acid, lactic acid, oxalic acid, succinic acid, fumaric acid, benzoic acid, benzenesulfonic acid, etc. and quaternary ammonium salts with alkyl halides such as methyl iodide, etc.

The compounds of the formula (I) and salts thereof can be prepared by the methods described in the specification of Unexamined Japanese Patent Application No. 113988/1983(Sho. 58) laid-open under the laying-open No. 6667/1985(Sho. 60) or Unexamined European Patent Application No. 84304292.0 published under Publication No. 0 130 077. Some of the formula (I) compounds are described in detail in the Examples of the above specifications, and some novel compounds are described in detail in the specification of the present invention.

As a result of investigations on pharmacological activity of ω-(p-substituted phenoxy)-2,2-dimethylalkanoic acids, esters or salts thereof, the present inventors have found that the compounds shown by general formula (I) described above inhibit the growth of tumors susceptible to treatment with certain substituted phenoxy dimethyl alkanoic acids, esters or salts thereof, and extremely low toxicity.

As is evident from results of animal test using mice described later, the anti-tumor activity of the compounds represented by general formula (I) is excellent in showing excellent inhibition effect on various tumors such as Ehrlich solid tumor, MM-46 solid tumor, Meth A solid tumor, Ehrlich ascites tumor, etc. and their toxicity is extremely low. Therefore, the compounds of general formula (I) can be used as safe and potent agents which inhibit the growth of tumors which are susceptible to treatment by such compounds or as agents for inhibiting metastasis of tumors which are also susceptible to such treatment.

Of the compounds included in general formula (I) described above, representative examples are as follows.

Methyl 5-[p-[3-(1-imidazolyl)propoxy]phenoxy]-2,2-dimethylpentanoate (Compound A)

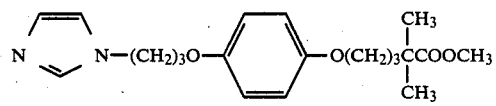

Ethyl 6-[p-[5-(1-imidazolyl)pentyloxy]phenoxy]-2,2-dimethylhexanoate (Compound B)

-continued

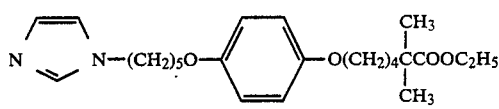

Ethyl 7-[p-[5-(1-imidazolyl)pentyloxy]phenoxy]-2,2-
dimethylheptanoate (Compound C) [hydrochloride]

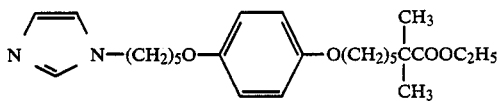

Ethyl/7-[p-[3-(1-imidazolyl)propoxy]phenoxy]-2,2-dimethyl-
heptanoate (Compound D)

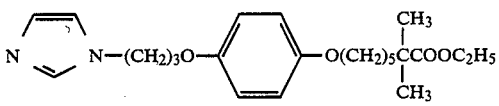

Methyl 7-[p-[3-(1-imidazolyl)propoxy]phenoxy]-2,2-
dimethylheptanoate (Compound E)

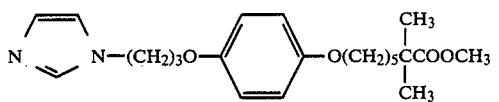

5-[p-[3-(1-Imidazolyl)propoxy]phenoxy]-2,2-dimethyl-
heptanoic acid (Compound F)

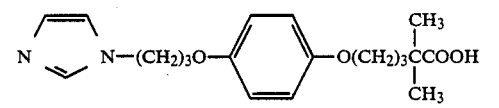

6-[p-[5-(1-Imidazolyl)pentyloxy]phenoxy]-2,2-dimethyl-
hexanoic acid (Compound G)

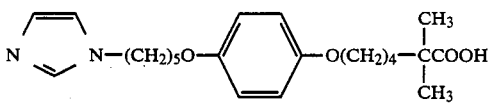

Methyl 7-[p-[3-(3-pyridyloxy)propoxy]phenoxy]-2,2-
dimethylheptanoate (Compound H)

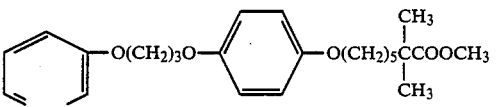

Methyl 2,2-dimethyl-5-[p-[3-(3-pyridyloxy)propoxy]-
phenoxy]pentanoate (Compound I)

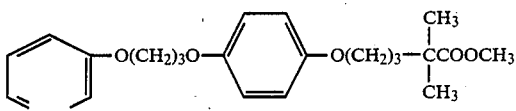

Ethyl 6-[p-[5-(2-pyridyloxy)pentyloxy]phenoxy]-2,2-dimethyl
hexanoate (Compound J)

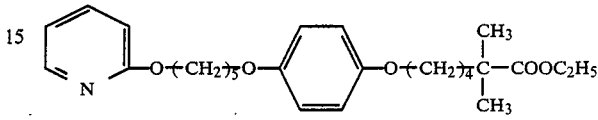

Of these compounds, Compounds H, I and J are novel compounds and their process for production will be described later.

(EXAMPLE)

Next, pharmacological activity, toxicity, etc. of the active components are shown below, together with test methods thereof.

Anti-Tumor Test (1) Anti-tumor test against Ehrlich solid tumor

Ehrlich tumor cells, $2 \times 10^6$, on Day 7 after intraperitoneal transplatation to ddY/SLC mice were subcutaneously transplanted in the left abdomen of ddY/SLC mice (5 week age, male), 10 each grouped into one. The active component was intraperitoneally or orally administered in a definite dose 24 hours after the transplantation, according to the schedule shown in Table 1 (A),(B) or (C). An effect of inhibiting growth of tumor was compared, by measuring the long diameter and short diameter of the tumor on 14, 20 and 21 Days after the transplantation, calculating the tumor size (mm$^2$) and determining a tumor growth inhibition rate of the group administered with the active component to the control group according to the following equation:

Growth inhibition rate (%) = $(C-T)/C \times 100$

T: mean tumor size (mm$^2$) in the active component-administered group
C: mean tumor size (mm$^2$) in the control group

TABLE 1

| Test Compound | Dose (mg/kg) | Route for Administration and Days Given | Day 14 Size of Tumor (mm$^2$) | Day 14 Growth Inhibition Rate (%) | Day 21 Size of Tumor (mm$^2$) | Day 21 Growth Inhibition Rate (%) |
|---|---|---|---|---|---|---|
| Compound B | 60 | intraperitoneal administration (1, 2, 3, 4, 7, 8, 10 & 13 Days) | 107.3 ± 54.6 | 25.7 | 323.3 ± 163.4 | 37.0 |
|  | 100 | intraperitoneal administration (1, 3, 7, 10, 13 & 14 Days) | 70.1 ± 33.8 | 51.4** | 315.3 ± 235.3 | 38.5 |
|  | 200 | p.o. (1, 2, 3, 4, 7, 8, 10 & 13 Days) | 48.7 ± 44.3 | 66.3** | 109.2 ± 133.5 | 78.7*** |
| 5-Fluorouracil | 25 | intraperitoneal administration (1, 2, 3, 4 & 7 Days) | 86.7 ± 35.1 | 40.0 | 217.8 ± 126.2 | 57.5** |
| Control |  |  | 144.4 ± 79.0 |  | 512.8 ± 271.3 |  |
| Compound C | 25 | intraperitoneal administration | 191.1 ± 88.8 | 18.1 | 363.1 ± 188.8 | 319* |

TABLE 1-continued

| Test Compound | Dose (mg/kg) | Route for Administration and Days Given | Day 14 Size of Tumor (mm²) | Day 14 Growth Inhibition Rate (%) | Day 21 Size of Tumor (mm²) | Day 21 Growth Inhibition Rate (%) |
|---|---|---|---|---|---|---|
| | 50 | (1, 2, 3, 5, 6, 7 & 9 Days) intraperitoneal administration | 135.0 ± 66.9 | 42.4** | 207.9 ± 139.7 | 61.0*** |
| | 100 | (1, 2, 3, 5. 6, 7 & 9 Days) intraperitoneal administration | 107.3 ± 46.7 | 54.2*** | 190.7 ± 69.1 | 64.2*** |
| Compound I | 25 | (1, 2, 3, 5, 6, 7 & 9 Days) intraperitoneal administration | 164.9 ± 96.2 | 29.6* | 336.6 ± 160.0 | 36.9* |
| | 50 | (1, 2, 3, 5, 6, 7 & 9 Days) intraperitoneal administration | 172.8 ± 82.9 | 26.2 | 369.1 ± 203.5 | 30.7* |
| | 100 | (1, 2, 3, 5, 6, 7 & 9 Days) intraperitoneal administration | 148.7 ± 66.8 | 36.5 | 290.2 ± 115.5 | 45.6** |
| 5-Fluorouracil | 25 | (1, 2, 3, 5, 6, 7 & 9 Days) intraperitoneal administration | 133.7 ± 61.1 | 42.9** | 306.8 ± 166.8 | 42.4** |
| Mitomycin | 1.0 | (1, 2, 3, 5, & 6 Days) intraperitoneal administration | 75.6 ± 31.5 | 67.7*** | 106.8 ± 62.2 | 80.0*** |
| Control | | (1, 2, 3, 5, & 6 Days) | 234.2 ± 82.1 | | 323.3 ± 141.5 | |
| Compound J | 50 | intraperitoneal administration (1, 2, 3, 4, 6, 7, 8, 9 Days) | 201.7 ± 48.2 | 20.9 | 344.7 ± 108.4 | 19.2 |
| | 100 | the same as above | 166.5 ± 65.3 | 34.7 | 263.5 ± 97.1 | 38.2 |
| 5-Fluorouracil | 12.5 | the same as above | 142.6 ± 36.9 | 44.1 | 280.6 ± 68.9 | 34.2 |
| | 25 | the same as above | 116.3 ± 44.0 | 54.4 | 252.3 ± 100.3 | 40.8 |
| Control | | | 255.1 ± 40.9 | | 426.5 ± 89.3 | |

*$p < 0.05$,
**$p < 0.01$
***$p < 0.001$ (2) Test against mouse mammalian MM-46 solid tumor MM-46 Tumor cells, $1 \times 10^6$, on Day 7 after intraperitoneal transplantation to C$_3$H/He/SLC mice were subcutaneously transplanted to the left abdomen of C$_3$H/He/SLC mice (5 week age, male) of 8 mice each being grouped in one (21 mice for the control group). The active component was orally administered in a definite dose 24 hours after the transplantation according to the schedule shown in Table 2. An effect of tumor growth inhibition was compared by measuring the long diameter and short diameter of the tumor on Days 14 and 21 after the transplantation, calculating the tumor size (mm²) and determining a tumor growth inhibition rate of the active component-administered group to the control group.

(3) Anti-tumor test against methyl cholanthrene-induced Meth A solid tumor:

Meth A tumor cells, $1.5 \times 10^6$, on Day 7 after intraperitoneal transplantation to Balb/C/SLC mice were subcutaneously transplanted to the left abdomen of Balb/C/SLC mice (5 week age, male) of 8 mice each being grouped in one (16 mice for the control group). The active component was orally administered in a definite dose 24 hours after the transplantation according to the schedule shown in Table 3. An effect of tumor growth inhibition was compared by measuring the long diameter and short diameter of the tumor on Days 15 and 21 after the transplantation, calculating the tumor size (mm²) and determining a tumor growth inhibition rate of the active component-administered group to the control group.

TABLE 2

| Test Compound | Dose (mg/kg) | Route for Administration and Days Given | Day 14 Size of Tumor (mm²) | Day 14 Growth Inhibition Rate (%) | Day 21 Size of Tumor (mm²) | Day 21 Growth Inhibition Rate (%) |
|---|---|---|---|---|---|---|
| Compund B | 100 | p.o. (1-9 Days) | 150.1 ± 52.1 | 40.4*** | 149.4 ± 84.8 | 55.8** |
| | 200 | " | 147.9 ± 56.2 | 41.3*** | 147.5 ± 65.3 | 53.4** |
| | 400 | " | 131.5 ± 55.2 | 47.8*** | 157.4 ± 104.0 | 53.4** |
| Tetrahydrofuryl-5-fluorouracil | 50 | " | 216.0 ± 55.1 | 14.2 | 247.0 ± 101.8 | 26.9 |
| | 100 | " | 214.8 ± 55.6 | 14.7 | 250.1 ± 92.9 | 26.0 |
| Control | | | 251.9 ± 71.2 | | 338.0 ± 151.6 | |

*$p < 0.05$,
**$p < 0.01$,
***$p < 0.001$

TABLE 3

| Test Compound | Dose (mg/kg) | Route for Administration and Days Given | Day 15 | | Day 21 | |
|---|---|---|---|---|---|---|
| | | | Size of Tumor (mm²) | Growth Inhibition Rate (%) | Size of Tumor (mm²) | Growth Inhibition Rate (%) |
| Compound B | 100 | p.o. (1–8 Days) | 163.0 ± 41.9 | 27.5 | 387.9 ± 101.8 | 18.8 |
| | 200 | " | 124.5 ± 6.02 | 46.4** | 290.8 ± 100.9 | 39.2* |
| | 400 | " | 104.4 ± 56.9 | 53.6** | 279.3 ± 152.1 | 41.6** |
| Tetrahydrofuryl-5-fluorouracil | 50 | " | 123.4 ± 69.99 | 45.1* | 235.8 ± 124.4 | 50.7** |
| | 100 | " | 93.1 ± 5.03 | 58.6** | 264.4 ± 110.6 | 44.7** |
| Control | | | 224.6 ± 89.8 | | 477.7 ± 189.8 | |

*$p < 0.05$,
**$p < 0.01$ (4) Anti-tumor effect against Ehrlich ascites tumor:

Ehrlich tumor cells, $1 \times 10^6$, on Day 7 after intraperitoneal transplantation to ddY/SLC mice were intraperitoneally transplanted to ddY/SLC (5 week age, male) of 10 mice each being grouped in one. The active component was intraperitoneally administered in a definite dose 24 hours after the transplantation according to the schedule shown in Table 4. An effect of tumor growth inhibition was evaluated by a percentage of the median survival day of the administered group versus that of the control group, according to the following equation.

$$T/C\% = T/C \times 100$$

T: median survival day of the administered group
C: median survival day of the control group

TABLE 4

| Test Compound | Dose (mg/kg) | Route for Administration and Days Given | Median Survival Day | T/C (%) | No. of 40-day Survivors |
|---|---|---|---|---|---|
| Compound B | 15 | intraperitoneal (1–9 Days) | 16.0 | 106 | 0/8 |
| | 30 | " | 22.5 | 150.0 | 1/8 |
| | 60 | " | 21.5 | 143.3 | 2/8 |
| | 100 | intraperitoneal administration (1, 3, 6, 8 & 10 Days) | 26.5 | 176.7 | 2/8 |
| 5-Fluorouracil | 25 | intraperitoneal administration (1–9 Days) | 24.5 | 163.3 | 0.8 |
| Control | | | 15.0 | 100 | 0/10 |

(5) Anti-tumor test against mice mammary cancer MM-46 ascites tumor:

MM-46 tumor cells, $1 \times 10^6$, on Day 7 after intraperitoneal transplantation to C₃H/He/CRJ mice (5 week age, male) of 10 mice each being grouped in one. The active component was intraperitoneally administered in a definite dose 24 hours after the transplantation according to the schedule shown in Table 5. An effect of tumor growth inhibition was evaluated by a percentage of the median survival time of the administered group versus that of the control group, according to the following equation.

$$T/C\% = T/C \times 100$$

T: median survival day of the administered group
C: median survival day of the control group

TABLE 5

| Test compound | Dose (mg/kg) | Route of Administration and Days Given | Median Survival Day | T/C (%) | Survivors (90 days) |
|---|---|---|---|---|---|
| Compound B | 6.25 | intraperitoneal administration (1, 2, 3, 4 and 6 Days) | 7.0 | 93.3 | 0/10 |
| | 12.5 | | 7.0 | 93.3 | 0/10 |
| | 25 | | 8.5 | 113.3 | 0/10 |
| | 50 | | 34.0 | 453.3 | 0/10 |
| | 100 | | 49.0 | 653.3 | 1/10 |
| | 200 | | 18.5 | 246.7 | 0/10 |
| 5-Fluorouracil | 6.25 | | 16.0 | 213.3 | 0/10 |
| | 12.5 | | 17.0 | 226.7 | 0/10 |
| | 25 | | 20.0 | 266.7 | 0/10 |
| Control | | | 7.5 | | 0/10 |

It is known that the value of an animal tumor screen depends on its ability to select new drugs with efficacy against human tumors. It is also known that some rodent tumors (for example, L1210, B-16, etc.) would have predicted the clinical activity of most of the established anticancer drugs.

The active ingredients of the present invention inhibit transplanted mammalian tumor growth (for example, liver cancer, mammary cancer, etc.) in mammals when administered orally or intraperitoneally in amounts ranging from about 12.5 mg to about 400 mg per kilogram of body weight per day.

(6) Inhibition of tumor metastasis:

(a) Inhibition of spontaneous metastasis (to the lymph node) of liver cancer (MH-134) cells in mice MH-134 tumor cells, $1 \times 10^6$, on Day 7 after intraperitoneal transplantation to C$_3$H/He/SLC mice were transplanted to the right leg. On the 11th day after the transplantation, the right leg portion wherein the cancer cells were transplanted were cut off. The test compounds were administered orally in a definite dose 24 hours after the transplantation. In order to confirm metastasis-inhibiting effect, on 20th day of the transplantation the mice were anatomised to observe the metastasis to the lymph node in the inguinal portion.

Metastasis-inhibition rate (%) =

$$1 - \frac{\text{metastasis occurence rate (\%) administered of the/group}}{\text{metastasis occurence rate (\%) of the control group}}$$

(b) Inhibition of experimental metastasis (to the lung) of melanoma BL-6 in mice:

BL-6 cancer cells, $5 \times 10^4$, were inoculated into the tail veins of male BDF$_1$/SLC mice (6 week age) of 6 mice each being grouped in one (13 mice for the control group). The test compounds were administered orally in a definite dose 24 hours after the inoculation. In order to see metastasis-inhibitory effect, on 22th day after the inoculation, the mice were anatomised to observe the metastasis to the lungs. The degree of metastasis was evaluated by the number of pulmonary nodules.

$$\text{Metastasis (to the lung) inhibition rate (\%)} = \frac{C - T}{C} \times 100$$

T: Median number of pulmonary nodules of the administered group
C: Median number of pulmonary nodules of the control group TABLE 6(b)

| Test compound | Dose (mg/kg) | Route of administration and days given | The number of pulmonary nodules range | The number of pulmonary nodules median | Pulmonary metastasis-inhibition rate (%) |
|---|---|---|---|---|---|
| Compound B | 200 | Oral administration (1, 2, 3, 5, 6, 7, 8, 9 and 10 days) | 1–20 | 10.5 | 50.0 |
|  | 400 | Oral administration (1, 2, 3, 5, 6, 7, 8, 9 and 10 days) | 1–14 | 6.5 | 69.0 |
| Futoraful | 50 | Oral administration (1, 2, 3, 5, 6, 7, 8, 9 and 10 days) | 1–49 | 13.5 | 35.7 |
|  | 100 | Oral administration (1, 2, 3, 5, 6, 7, 8, 9 and 10 days) | 1–16 | 6.5 | 69.0 |
| Control |  |  | 3–87 | 21.0 | 0 |

Further, the weight of the lymph node metastasis tumor in the inguinal portion of anatomised mice was measured.

Growth inhibition rate (%) of metastasis tumor (%) =

$$1 - \frac{\text{mean weight of the tumor of the administered group}}{\text{mean weight of the tumor of the control group}}$$

From the above results, it is apparent that the compounds of this invention have effects of inhibition of tumors or inhibition of metastasis of the various tumors susceptible to treatment with the compounds of formula (I). Thus, the compounds of the formula (I) is expected to be useful for treatment of cancer metastasis.

(7) The effectiveness against mouse tumor cells and human tumor cells (in vitro cytotoxicity test)

(a) against mouse tumor cells:

TABLE 6(a)

| Test compound | Dose (mg/kg) | Route of administration and days given | Metastasis-inhibition rate (%) | Growth inhibition of the metastasis tumor (%) |
|---|---|---|---|---|
| Compound B | 100 | oral administration (1, 3, 5, 7, 9, 11, 13 and 15 days) | 8.5 | 33.8 |
|  | 200 | oral administration (1, 3, 5, 7, 9, 11, 13 and 15 days) | 41.2 | 79.4 |
|  | 400 | oral administration (1, 3, 5, 7, 9, 11, 13 and 15 days) | 73.9 | 80.4 |
| 5-Florouracil | 50 | oral administration (1, 3, 5, 7, 9, 11, 13 and 15 days) | 17.7 | 48.7 |
|  | 100 | oral administration (1, 3, 5, 7, 9, 11, 13 and 15 days) | 41.2 | 74.2 |

A suspension of cells in a culture medium was transferred into wells in a microplate in an amount of $1 \times 10^5$ cell/well. Test sample diluted with a culture medium was added to the suspension in each well, and the mixture was incubated on the medium at 37° C. for 3 days in atmosphere of air containing 5% carbon dioxide. Thereafter, the incubated cells were recovered from the microplate and the number of live cells was counted by the dye exclusion test using a 0.5% solution of trypan blue and by using a hemocytometer. The cytotoxicity effects against various mice tumor cells were evaluated by the mean dose producing 50%-killing of tumor cells ($IC_{50}$). The cytotoxicity data for the test compound and that of 5-fluorouracil are given in Table 7(a).

TABLE 7 (a)

|  | $IC_{50}$ (μg/ml) | |
| --- | --- | --- |
|  | Test compound (Compound B) | 5-fluorouracil |
| L-1210 | 1.9 | 0.06 |
| Ehrlich (carcinoma) | 0.5 | 0.05 |
| MM 46 (mammary cancer) | 0.7 | — |
| MH 134 (liver cancer) | 2.2 | 0.009 |
| Meth A (methylcholanthrene-induced cancer) | 0.8 | 0.1 |

(b) against human tumor cells: A suspension of cells in a culture medium was transferred into wells in a microplate in an amount of $5 \times 10^4$ cell/well. Test sample diluted with a culture medium was added to the suspension in each well, and the mixture was incubated at 37° C. for 3 days an atmosphere of air containing 5% carbon dioxide. After skimming, sticking cells were dyed with crystalviolet for 10 minutes. After washing with water, 1% sodium lauryl sulfate solution was added to each well, and the absrobancy (optical density) at 540 m was measured. "% inhibition" was calculated from the following equation.

$$\% \text{ inhibition} = \left(1 - \frac{\text{optical density (administered group)}}{\text{optical density (control group)}}\right).$$

The cytotocicity effects against various human tumor cells were evaluated by the mean dose producing 50%-killing of tumor cells ($IC_{50}$).

TABLE 7 (b)

|  | $IC_{50}$ (μg/ml) | |
| --- | --- | --- |
|  | Test compound (Compound B) | 5-fluorouracil |
| KB (nasal cavity & pharynx cancer) | 1.15 | 1.75 |
| Hela (uterine cancer) | 2.05 | |
| Bowes (melanoma) | 1.00 | 0.61 |
| ACHN (kidney cancer) | 2.30 | 0.10 |

Toxicity Test

The active component was orally administered to ddY mice (mean body weight of 35 g, male). No example of death was noted up to the dose of 5,000 mg/kg. Accordingly, the acute toxicity of Compound B is greater than 5,000 mg/kg.

(Effects)

From the foregoing test results, ω-(p-substituted phenoxy)-2,2-dimethylalkanoic acids, esters or salts thereof possess excelent anti-tumor activity but have low toxicity and therefore, effective for use in inhibiting the growth of tumors susceptible to treatment by said acids, esters or salts.

Clinical dose of the tumor inhibiting agent of the present invention is daily 500 to 2,000 mg for adults, preferably 800 to 1,200 mg, in the case of oral administration or in a suppository form. The dose is given once or divided into 2 to 4 smaller doses. The dosage is appropriately varied depending on condition of patient, combination use with other agents, age, etc.

In the case of oral administration, medical preparations are in the form of tablets, capsules, granules or syrups. In the case of perenteral administration, suppositories or injections are applicable. As excipients used for preparation of oral administration, there are lactose, starch, sucrose, talc, magnesium stearate, sorbitol, microcrystalline cellulose, carboxymethyl cellulose, hydroxypropyl cellulose, etc. As bases used for preparation of suppositories, there are polyethylene glycol, lanolin, cocoa butter, Witep Sol (trademark, manufactured by Dynamit Nobel Co., Ltd.).

Hereafter an example of preparing capsules is shown below.

| Preparation of capsules: | |
| --- | --- |
| Compound B | 200 mg |
| Lactose | 205 mg |
| Crystalline cellulose | 50 mg |
| Hydroxypropyl cellulose | 15 mg |
| Starch | 25 mg |
| Magnesium stearate | 5 mg |
| | 500 mg |

According to the composition described above, the main ingredient, lactose and crystalline cellulose are mixed and an aqueous solution of hydroxypropyl cellulose is added thereto. After the mixture is kneaded, grained and dried, magnesium phosphate is added thereto and mixed. The mixture is filled up in No. 1 gelatin capsules to prepare capsules.

Preparation of Compound H:

After 110 mg of sodium hydride (60% suspension in mineral oil) was washed with dry benzene, 10 ml of dry dimethylformamide was added thereto and 264 mg of 3-hydroxypyridine was further added to the mixture with stirring. After vigorous foaming was discontinued, the suspension was heated at 80° C. for 30 minutes with stirring and then cooled to room temperature. A solution of 870 mg of methyl 7-[p-(3-bromopropoxy)-phenoxy]-2,2-dimethylheptanoate in 10 ml of dry dimethylformamide was added to the suspension followed by stirring at 60° C. for 5 hours. Thereafter the solvent was removed from the reaction solution under reduced pressure. The remained oily substance was dissolved in benzene, washed with an aqueous saturated hydrogen sodium carbonate solution, water and a saturated saline solution in this order and then dried over anhydrous sodium sulfate. After drying, the solvent was distilled off under reduced pressure. The remaining oily substance was subjected to silica gel column chromatography and the product was eluted out using as an eluent chloroform-methanol solution (50:1). The solvent was distilled off from the eluate under reduced pressure to give the desired methyl 7-[p-[3-(3-pyridyloxy)propoxy]phenoxy]-2,2-dimethylheptanoate as an oily substance.

NMR spectra (CDCl₃) (internal standard TMS) δ(ppm);

1.16 (6H, s, 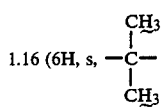

1.2~1.8 (8H, m, 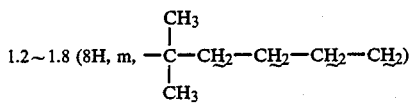

2.33 (2H, quin, J = 6 Hz, O—CH₂—CH₂—CH₂—O)

3.64 (3H, s, 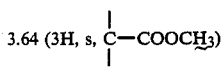

3.86 (2H, t, J = 6 Hz, 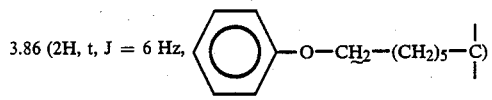

4.10 (2H, t, J = 6 Hz, 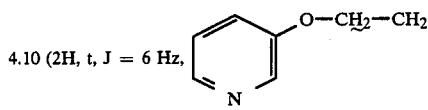

4.18 (2H, t, J = 6 Hz, 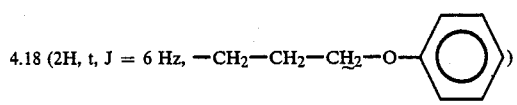

6.79 (4H, s, 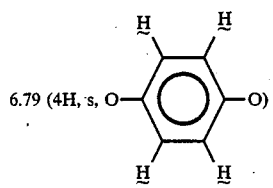

7.16 (2H, m, 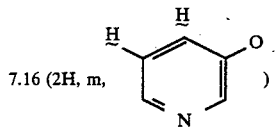

8.16 (1H, t, J = 2 Hz, 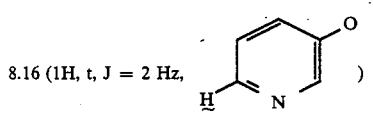

8.28 (1H, t, J = 2 Hz, 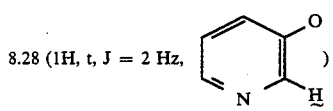

Preparation of Compound I

Using as a starting material methyl 5-[p-[(3-bromopropoxy)phenoxy]-2,2-dimethylpentanoate in place of methyl 7-[p-(3-bromopropoxy)phenoxy]-2,2-dimethylheptanoate in Preparation of Compound H, similar reaction and treatment were conducted to give the desired methyl 2,2-dimethyl-5-[p-[3-(3-pyridyloxy)-propoxy]phenoxy]pentanoate as an oily substance.

NMR spectra (CDCl₃) (internal standard TMS) δ(ppm);

1.22 (6H, s, 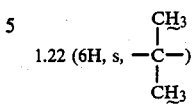

1.5~1.8 (4H, m, 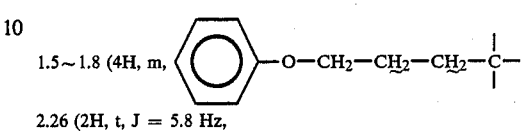

2.26 (2H, t, J = 5.8 Hz, 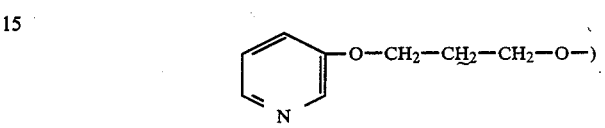

3.68 (3H, s, —COOCH₃)

3.88 (2H, m, 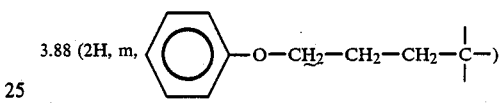

4.12 (2H, t, J = 5.8 Hz, 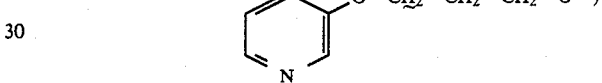

4.22 (2H, t, J = 5.8 Hz, 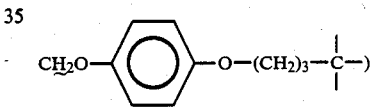

6.84 (4H, s, 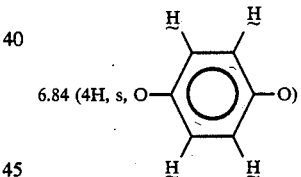

7.2 (2H, m, 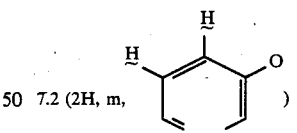

8.23 (1H, t, J = 1.8 Hz, 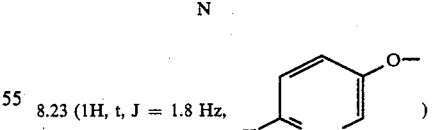

8.34 (1H, s, 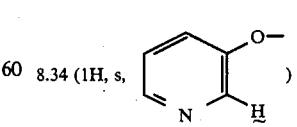

Preparation of Compound J

Into 5 ml of dry dimethylformamide containing 150 mg of sodium hydride (60% suspension in mineral oil) was added 292 mg of 2-hydroxypyridine. After stirring the mixture at room temperature for 15 minutes, 1.2 g of ethyl 6-[p-(5-bromopentyloxy)phenoxy]-2,2-dimethylhexanoate was added thereto. The mixture was stirred at room temperature for 12 hours, and thereafter the solvent was removed from the reaction solution under reduced pressure. The remaining oily substance was dissolved in chloroform, washed with water, and then dried over anhydrous magnesium sulfate. After drying, the solvent was distilled off under reduced pressure. The remaining oily substance was subjected to silica gel column chromatography and the product was eluted out using as an eluent chloroform-methanol (99:1). The solvent was distilled off from the eluate under reduced pressure to give the desired ethyl 6-[p-[5-(2-pyridyloxy)pentyloxy)phenoxy]-2,2-dimethylhexanoate as an oily substance (495 mg).

NMR spectra (CDCl$_3$) δ(ppm) 1.16 (6H, s) 6.10 (1H, dd), 1.22 (3H, t) 6,52 (1H, dd), 3.6 - 4,3 (6H, m) 6,76 (4H, s), 4.10 (2H, q).

Mass spectrum M+m/z 443.

We claim:

1. A method of inhibiting the growth of tumors in a mammal wherein the growth of said tumors is susceptible to treatment by a compound selected from the group consisting of ethyl 6-[p-{5-(1-imidazolyl)pentyloxy}phenoxy]-2,2-dimethylhexanoate hydrochloride,
   ethyl 7-[p-[5-(1-imidazolyl)pentyloxy]phenoxy]-2,2-dimethylheptanoate, and
   ethyl 6-[p-[5-(2-pyridyloxy)pentyloxy]phenoxy]-2,2-dimethylhexanoate, which comprises administering to said mammal an anti-tumor effective amount of said compound.

2. The method of claim 1 for inhibiting the growth of tumors in a mammal wherein the growth of said tumors is susceptible to treatment by ethyl 6-[p-{5-(1-imidazoyl)pentyloxy}phenoxy]-2,2-dimethylhexanoate hydrochloride, which comprises administering to said mammal an anti-tumor effective amount of said compound.

3. The method of claim 1 for inhibiting the growth of tumors in a mammal wherein the growth of said tumors is susceptible to treatment by ethyl 7-[p-[5-(1-imidazolyl)pentyloxy]phenoxy]-2,2-dimethylheptanoate, which comprises administering to said mammal an anti-tumor effective amount of said compound.

4. The method of claim 1 for inhibiting the growth of tumors in a mammal wherein the growth of said tumors is susceptible to treatment by ethyl 6-[p-[5-(2-pyridyloxy)pentytloxy]phenoxy]-2,2-dimethylhexanoate, which comprises administering to said mammal an anti-tumor effective amount of said compound.

* * * * *